United States Patent [19]
Dory

[11] Patent Number: 5,665,054
[45] Date of Patent: Sep. 9, 1997

[54] CONTROL METHOD FOR HYPERTHERMIA TREATMENT APPARATUS USING ULTRASOUND

[75] Inventor: Jacques Dory, Villiers-sur-Morin, France

[73] Assignee: Technomed Medical Systems S.A., Vaulx-en-Velin, France

[21] Appl. No.: 374,432

[22] Filed: Jan. 19, 1995

[30] Foreign Application Priority Data

Jan. 27, 1994 [FR] France ................................. 94 00904

[51] Int. Cl.$^6$ ............................................. A61N 7/02
[52] U.S. Cl. ............................. 601/3; 601/2; 128/660.03
[58] Field of Search ................ 601/2–4; 128/660.03, 128/240, 349; 607/97

[56] References Cited

U.S. PATENT DOCUMENTS

| 4,938,217 | 7/1990 | Lele. | |
|---|---|---|---|
| 5,178,135 | 1/1993 | Uchiyama et al. | 128/240 |
| 5,193,527 | 3/1993 | Schafer | 128/240 |

FOREIGN PATENT DOCUMENTS 0226821  7/1987  European Pat. Off..

OTHER PUBLICATIONS

Emad S. Ebbini, "A Spherical–Section Ultrasound Phased Array Applicator for Deep Localized Hyperthermia", *IEEE Transaction Biomedical Engineering*, vol. 38, No. 7, Jul. 1991, pp. 634–643.

*Primary Examiner*—Marvin M. Lateef
*Assistant Examiner*—Eleni Mantis Mercader
*Attorney, Agent, or Firm*—Welsh & Katz, Ltd.

[57] ABSTRACT

A method for controlling an ultrasonic hyperthermia treatment apparatus is disclosed. The hyperthermia treatment apparatus utilizes ultrasound that is focused at a focal spot. The position of the focal spot relative to the transducer is varied, where the peak power of the focal spot and the degree of overlap between the various positions of the focal spot are such that the energy radiated during a shot at each point in the region scanned by the variation of the position of the focal spot represents an equivalent focal spot where the energy applied to the object to be treated is substantially equal to the energy needed to destroy the cell tissue.

20 Claims, 5 Drawing Sheets ns3-3qf
5,665,054

CONTROL METHOD FOR HYPERTHERMIA TREATMENT APPARATUS USING ULTRASOUND

BACKGROUND OF THE INVENTION

This invention relates to a method for controlling an ultrasonic hyperthermia treatment apparatus having a transducer with a plurality of piezoelectric elements each excitedly an electrical signal, in which ultrasound is focused at a focal spot and the position of said focal spot is varied with respect to the transducer at a speed that is higher than the speed at which thermal energy diffuses away from the area being treated.

The invention also provides a hyperthermia treatment apparatus including a transducer with a plurality of piezoelectric elements excited by a plurality of electrical excitation signals, with means for variably phasing each one of said electrical excitation signals.

The fact that ultrasonic waves, referred to generally as ultrasound, can be propagated within the human body and also can be easily focused is used in medicine for acting on internal structures from an external point in non-invasive therapy without the need for surgical intervention. The ultrasonic waves are focused into a specific region referred to as the focal point or focal spot. For the purposes of treatment, the focal point is brought to the region to be treated.

Hyperthermia treatment with focusing of ultrasound leads to local heating of tissue at the focal point with the consequent destruction thereof.

Known apparatus for carrying out hyperthermia treatment is described, for example in European Patents EP-A-0 162 735 (semi-spherical cup reflector and fixed focal spot of some 2 or 3 mm diameter), EP-A-0 370 841 (mechanically movable transducer), or EP-A 0 194 897 (scanning of treatment zone by mechanically shifting the transducer). A more complete description of these various devices and their disadvantages is given in French patent application No. 94.00904 (priority document for this present application), the contents of which are incorporated herein by reference.

An article by Ebbeni et al entitled "A spherical section ultrasound phased array for deep localisation hyperthermia", IEEE Transactions on Biomedical Engineering, vol. 38, no. 7, Jan. 7, 1991, pages 634–643 describes the results of computer simulation of transmission of ultrasound by a spherical-section array incorporating a plurality of piezoelectric elements. In this article, it is suggested to move the focal spot by varying the amplitude and phase of the various piezoelectric elements in order to irradiate a plurality of control points arranged on a circle, or on two concentric circles. It is however considered as preferable in this document to directly generate an ultrasound field incorporating the plurality of control point.

U.S. Pat. No. 4,938,217 discloses a hyperthermia device comprising a transducer having a plurality of piezoelectric elements which combines mechanical movement of the transducer and modification of the depth of the focal spot or its distance from the transducer by appropriately phasing the excitation signals, this being referred to as apodization. In this patent, varying the focal length during rotation of the transducer enables irregularly-shaped regions to be scanned.

These various known devices have certain disadvantages.

It is difficult to synthesise focal spots of large size as in EP-A-0,194,897, or which exhibit a plurality of peaks as in the Ebbeni et al article: firstly, this implies complex phase and amplitude calculations for the excitation signals and, secondly, in the case of actual treatment apparatus having a reasonable number of piezoelectric elements, this creates irregularities around the focal spot which can cause lesions.

If, as opposed to this, focal spots of reduced dimension are employed, it becomes difficult to treat large volumes. Mechanical scanning of the treatment zone, through movement of the transducer (EP-A-0,194,897 or U.S. Pat. 4,938, 217) requires the presence of mechanical means for moving the transducer, which leads to cumbersome and complicated equipment. Moreover, numerous shots are necessary and if the region requiring treatment is itself moving due to the patient's breathing, the points of impact are distributed in a somewhat random fashion within the volume theoretically scanned. The treatment region cannot be fully scanned (presence of gaps), and some points of impact can even fall outside this region.

Electronically steering the focal spot using apodization, as suggested in the article by Ebbeni et al or in U.S. Pat. No. 4,938,217 is a technique that is complicated to implement: it is in fact difficult to modify the peak power of the ultrasonic waves delivered by each individual piezoelectric element particularly when very rapid changes are needed.

One further problem involves the question of how to distribute the energy within the focal spot. In the article by Ebbeni et al, it is proposed, in order to determine the energy necessary to attain and maintain a certain level of hyperthermia, to calculate a spatio-temporal mean within the volume of the tumour of the energy deposited at the control points. This type of approach can only be usefully applied in the case of so-called "conventional" hyperthermia, i.e. for large volumes and moderate temperatures (43° to 45° C.). U.S. Pat. No. 4,938,217 simply states that it is desirable to obtain a uniform temperature within the tumour, and to avoid excessive overheating. There is no indication in this document of how to choose the energy level at the focal spot or at the various points within the region to be treated. In known devices, losses through diffusion of heat energy represent a significant portion of the energy delivered to the patient and a high percentage of the energy radiated is not used for cell destruction. This is problematic as an excess of energy radiated can lead to lesions as a result of burning, either of internal tissue or of the skin.

SUMMARY OF THE INVENTION

The present invention provides a solution to these various disadvantages. It resolves the problem of destroying a region to be treated by hyperthermia with a minimal energy loss, regardless of the shape of the region to be treated. It particularly applies to what is know as pyrotherapy, i.e. hyperthermia carried out at elevated temperatures (for example over 48° C.), enabling practically instantaneous cell destruction to be obtained.

The invention provides a method for controlling an ultrasonic hyperthermia treatment apparatus having a transducer with a plurality of piezoelectric elements each excited by an electrical signal, where the method includes emitting ultrasound focused to a focal spot and causing the position of the focal spot to vary with respect to the transducer or with respect to the means supporting the transducer during a shot. The speed of variation of the position of the focal spot with respect to the transducer or with respect to the means supporting said transducer is higher than the speed of diffusion of thermal energy in the region to be treated, in which the peak power of the focal spot and the degree of overlap between the various positions of the focal spot are such that, during a shot, the energy radiated at every point on the region scanned by varying the position of the focal spot with respect to the transducer or the means supporting the transducer, and constituting an equivalent focal spot, is substantially equal to the energy needed to destroy tissue cells in the region to be treated.

Due to this method, the amount of energy radiated during treatment is minimal, thus avoiding the danger of burning outside of the treated zone. Moreover, there is a guarantee that tissue destruction will occur.

In a preferred embodiment, variation of the position of the focal spot with respect to the transducer is solely due to variation in the relative phases of the electrical signals exciting said piezoelectric elements.

According to one preferred feature, the equivalent focal spot is homogeneously scanned during a shot.

This is particularly advantageous for the first shot.

Alternatively, the equivalent focal spot is scanned in a non-homogeneous manner during a shot in order to supplement energy supplied during one or several preceding shots.

This enables account to be taken of diffusion or spreading of heat energy or the deposition of energy in neighboring layers.

According to one preferred feature, the ultrasound energy is delivered, during a shot, in the form of wave trains separated by blank intervals, and the position of said focal spot varies with respect to the transducer during the blank intervals.

In an alternative embodiment, the ultrasound is delivered, during one shot, in the form of continuous wave trains and the position of said focal spot varies with respect to the transducer without delivery of ultrasound being interrupted.

These two embodiments are also simple to implement.

According to another feature, the focal spot has an elongated shape and is displaced with respect to the transducer substantially along its longitudinal direction.

The invention also provides hyperthermia treatment apparatus having a transducer with a plurality of piezoelectric elements excited by a plurality of electrical excitation signals, and means for shifting the phase of said electrical excitation signals, and further including a plurality of transmitters each transmitting an electrical excitation signal to one of said piezoelectric elements. Also included is a source of a high-frequency pilot signal supplied from a common pilot signal to each of the transmitters, and an address generator. The means for shifting the phase of said signals within each one of said transmitters is a function of an address received from the address generator.

In one embodiment of the hyperthermia treatment apparatus, in each one of said transmitters, the means for shifting the phase of the pilot signal includes a shift register and memory means controlling the shift register as a function of the address received from said address generator, where the memory means is pre-programmed as a function of the position of the transmitter in which they are located.

In this case, each one of the shift registers is able to produce shifting of the phase of the pilot signal varying in one-sixteenth of a period steps. In an alternative embodiment, each shift register can produce shifting of the phase of the pilot signal varying in steps of one-eighth of a period.

The advantages and features of the invention will become more clear from the description that follows provided solely by way of example.

DETAILED DESCRIPTION OF PREFERRED EMBODIMENTS

Figure 1:
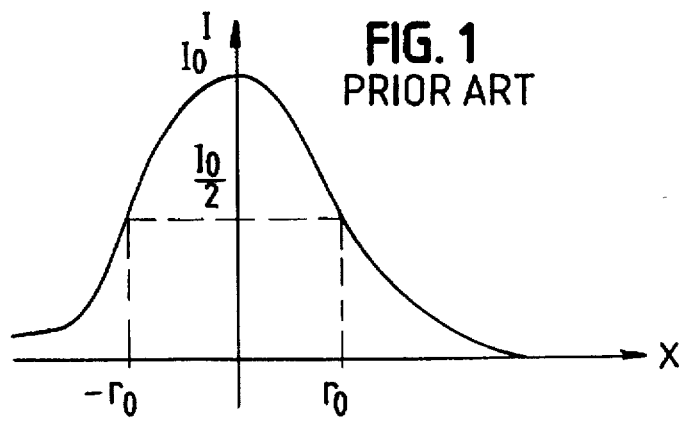
FIG. 1 shows the shape of the power intensity at the focal spot in a device according to the prior art.

FIG. 1 shows the shape of the curve of power intensity at the focal point in a device according to the prior art, such as described in European Patent application 0,370,841. This apparatus includes a power transducer in the form of a semi-spherical dish for concentrating ultrasound to a focal point situated at the geometrical center of the semi-spherical dish. Because of this specific shape, the focus exhibits symmetry of revolution about the axis of symmetry of the semi-spherical dish. FIG. 1 shows power intensity at the focus, along a straight line passing therethrough and perpendicular to the axis of symmetry of the semi-spherical dish. The x-axis shows the distance from the axis of symmetry of the semi-spherical dish and the y-axis shows ultrasound power intensity.

The curve in FIG. 1 is bell-shaped, with ultrasound power intensity dropping off progressively from the center of the focal spot down to the periphery. It is generally considered that the diameter of the focal spot corresponds to a circle of radius $r_o$, centered on the axis of symmetry of the ultrasound beam, inside which the ultrasound power level is higher than half the power level $I_o$ along the beam axis (6 dB diameter).

Bearing in mind the problems associated with movements of the region to be treated, in prior art devices, the power level of the ultrasound beam and the duration of firing are chosen so that the regions to be treated situated inside the focal spot were completely destroyed in one single shot. Beam intensity is thus chosen whereby, at the edge of the focal spot, the beam intensity $I_o/2$ ensures the tissue to be treated is destroyed in a single shot.

Further inside the focal spot, the ultrasound beam intensity is higher than $I_o/2$, and the part that is above $I_o/2$ corresponds to unnecessary energy. Similarly, outside of this focal spot, the energy does not have a non-zero value while being insufficient to destroy the cells. This energy also is wasted energy. Such excess energy increases the risk of skin burns to the patient. Moreover, it has the effect of increasing tissue temperature around the focal spot. If energy is applied too quickly to tissue, this can lead to lesions being produced outside the treatment region.

In prior art systems using power diagrams of this type, total energy radiated is about 2.5 times that theoretically necessary to destroy the tissues inside the focal spot.

By way of illustration, in a device such as the one described in European Patent application 0.370,841, the focal spot has a diameter of about 2 mm. After a short period referred to as the settling or stabilization time, the temperature inside the spot ceases to increases as losses by heat transfer exactly compensate the supply of ultrasound energy. In the known device, this stabilization time is about 2 seconds for an acoustic power of around 10 kW. For an acoustic power of some 10 kW, those tissues located at the focal spot are destroyed by the ultrasound wave after a single shot during about 0.1 s. This period of time is below the stabilization time.

Figure 2:
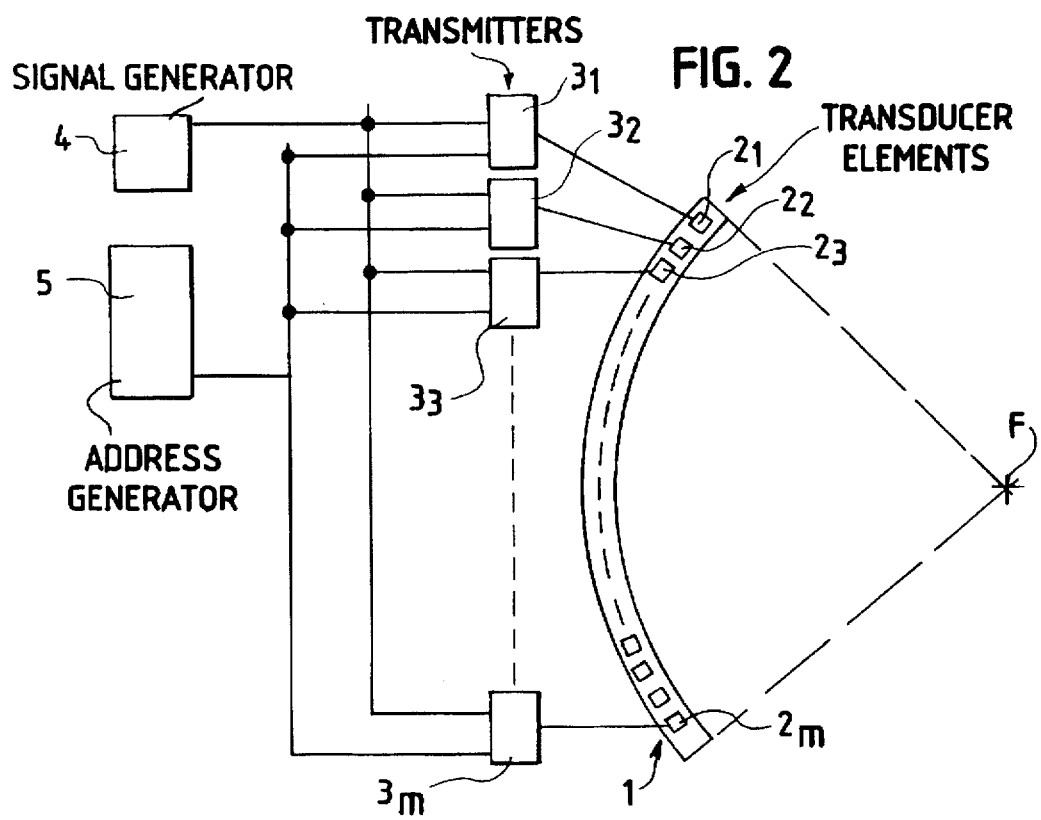
FIG. 2 is a schematic representation of apparatus for implementing the method according to the invention.

FIG. 2 schematically shows apparatus for implementing the method according to the invention. Like known devices, the apparatus in FIG. 2 includes a transducer 1 made up of a plurality, m, of piezoelectric elements $2_1, 2_2, \ldots 2_m$ each of which is excited by an electrical signal. In the diagram of FIG. 2, transducer 1 takes the form of a semi-spherical dish but the invention is not limited to this shape. The transducer could also consist of several individual parts each one including a plurality of piezoelectric elements.

Advantageously, the transducer is coupled to an imaging device, using, for example, ultrasound scanning or echography, as described in European patent 0,162,735. Transducer 1 also includes a device that is not shown allowing ultrasound coupling, for example consisting of a cavity integral with transducer 1, closed off by a flexible membrane and filled with a liquid.

The ultrasound waves delivered by the piezoelectric elements $2_1$ to $2_m$ are concentrated into a focal spot. In the case where the transducer is in the shape of a semi-spherical dish, the focal spot is located at the geometrical center F of said dish, when the excitation signals for the piezoelectric elements are all in phase. Each piezoelectric element $2_1 \ldots 2_m$ of transducer 1 is excited by a high-frequency electrical signal originating from a corresponding transmitter $3_1 \ldots 3_m$. The transmitters $3_1 \ldots 3_m$ receive, firstly, a high-frequency pilot frequency from generator 4 and, secondly, the signal from an address generator 5. The high-frequency pilot frequency generator 4 supplies a high-frequency signal constituting a common source for all the transmitters and will be described in more detail below. Operation of the address generator will be better understood with reference to the description for FIG. 3.

The apparatus in FIG. 2 further includes control means which are not shown, for controlling the operation of the high-frequency pilot signal generator 4 and address generator 5. These control means may be programmed by an operator.

Figure 3:
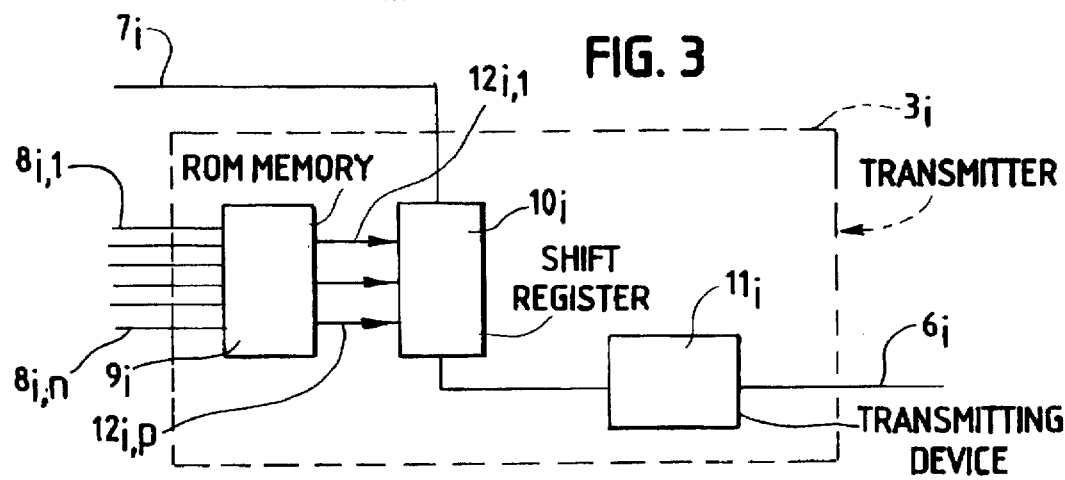
FIG. 3 shows one embodiment of the transmitter of the apparatus in FIG. 1.

FIG. 3 shows one embodiment of a transmitter $3_i$ of the apparatus in FIG. 2. Transmitter $3_i$ has the task of sending an electrical excitation signal to a piezoelectric element $2_i$ on line $6_i$. Transmitter $3_i$ receives a pilot signal from high-frequency pilot signal generator 4 on line $7_i$. It also receives an address signal from address generator 5 on a plurality, n, of lines $8_{i,1}$ to $8_{i,n}$.

Transmitter $3_i$ comprises memory means, for example a ROM memory $9_i$ (or any other type of memory), a shift register $10_i$ and a transmitting device $11_i$. ROM memory $9_i$ receives signals from address generator 5, on lines $8_{i,1}$ to $8_{i,n}$; it issues control signals to shift register $10_i$ on p lines $12_{i,1}$ to $12_{i,p}$. Shift register $10_i$ receives, on line $7_i$, the pilot signal from pilot signal generator 4 shown in FIG. 2. It sends a signal to transmitter device $11_i$ on line $13_i$. Transmitter device $11_i$ receives, on line $13_i$, the signal originating from shift register $10_i$ and sends, on line $6_i$, an electrical excitation signal to piezoelectric element $2_i$.

Implementation of the equipment described above is within the knowledge of those skilled in the art, using conventional components.

According to the invention, the position of the focal spot from transducer 1 varies during treatment. Variation in the position of the focal spot is obtained by varying the relative phases of the electrical excitation signals for the piezoelectric elements, as will now be explained.

High-frequency pilot signal generator 4 sends a pilot signal to all the transmitters $3_1$ to $3_m$. This signal is received in each transmitter $3_i$ by the shift register $10_i$. The signal received undergoes phase variation in the shift register. The phase-shifted signal is used to control transmission, by transmission device $11_i$, to the piezoelectric element $2_i$.

Moreover, address generator 5, for a given position of the focal spot, generates address signals on lines $8_{i,1}$ to $8_{i,n}$ corresponding to the desired position of the focal spot. These address signals are received, in each transmitter $3_i$, by ROM memory $9_i$. ROM memory $9_i$ delivers, in response to the address signal, control signals to the shift registers $10_i$.

ROM memory $9_i$ of each transmitter $3_i$ is programmed in advance as a function of the position of the corresponding piezoelectric element $2_i$, so as to supply shift register $10_i$ with control signals producing a phase variation $\delta\phi_i$ in the shift register. This phase variation is the variation necessary for piezoelectric element $2_i$ to position the focal spot at the desired position, as supplied by the address signals.

In one embodiment of the invention, the memory address is programmed in an address generator on n=13 bits. This makes it possible to scan over $2^n=8192$ positions for the focal spot, equivalent to 1024 positions in a plane perpendicular to the axis of the target, and at 8 different depths.

In this case, it is sufficient for the shift registers $10_i$ to have a precision of one sixteenth of a period: because of this, the integer p can be chosen to have a value of 4.

In the case of a semi-spherical dish-shaped transducer of a diameter of about 300 mm having a focal length of around 320 mm and 160 piezoelectric elements of 20 mm diameter, the focal spot has a 6 dB diameter of the order of 2 mm. Adopting a value p=4 for the shift registers makes it possible to obtain, in a plane perpendicular to the axis of symmetry of the semi-spherical dish, variation in the position of the focal spot with a pitch of the order of 0.5 mm.

It is also possible to employ a one-eighth of a period resolution for phase shifting. In this case, the phases of the piezoelectric element excitation signals vary in steps of one-eighth of a period. Integer p then has a value of 3.

The apparatus described with reference to FIGS. 2 and 3 thus makes it possible to vary the position of the focal spot with respect to transducer 1. According to the invention, said position is varied so as to constitute, during a shot, a region which is referred to herein as the equivalent focal spot.

Figure 4A:
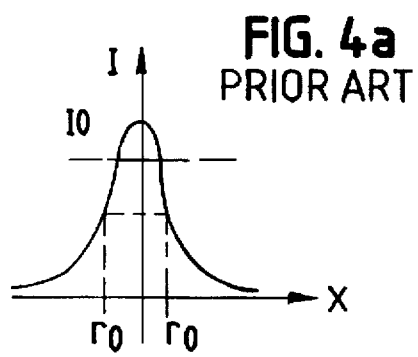
FIG. 4a shows the shape of the power intensity at the focal spot in a device according to the invention.

FIG. 4a shows the shape of the power intensity at the focal spot of a transducer of the type described above. The curve in FIG. 4a is the same as that in FIG. 1, with a different scale on the x-axis.

Figure 4B:
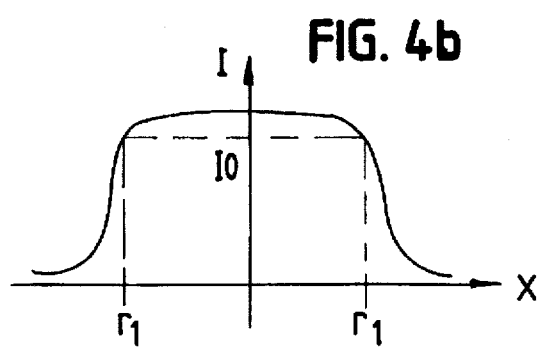
FIG. 4b shows the shape of the power, intensity at the equivalent focal spot in a device according to the invention.

FIG. 4b shows the shape of power intensity at the equivalent focal spot, obtained according to the invention.

We shall first describe an example of an embodiment of the invention in which a transducer having a 6 dB focal spot radius $r_o$ of about 1 mm is employed. During a shot, the position of the focal spot is varied with respect to the transducer, by moving the focal spot by a distance of the same order as its radius $r_o$, with a periodicity of the order of 1 ms.

To achieve this, high-frequency pilot signal generator 4 sends a periodic signal consisting of wave trains of a frequency of the order of 1 MHz with a duration of one millisecond, separated by a 5 microsecond blank interval. During each blank interval, the position of the focal spot can be changed using address generator 5. As the amplitude of the excitation signals delivered by high-frequency pilot signal generator source is always identical, and as apodization is not employed here, this 5 μs duration is sufficient for the memory means $9_i$ to receive the signals originating from the address generator for consequently commanding the shift registers $10_i$. The control means of the apparatus are programmed so as to sweep an equivalent focal spot having an area about 50 times that of the area of the focal spot, and having a disk shape. This equivalent focal spot is swept over a period of the order of 0.1 s, by varying the position of the focal spot 100 times. When sweeping an equivalent focal spot having a disk shape, the scanned surface area has a diameter of the order of 15 mm ($\sqrt{50\times2}$ mm); overlap between the various neighbouring positions of the focal spot is of the order of 50%. Conduction away of heat during this period is negligible and the shape of power intensity within the equivalent focal spot, after the end of this 0.1 s period is shown in FIG. 4b on the same scale as FIG. 4a.

As can be seen from FIG. 4b, because of the variation in the position of the focal spot over time during the shot, the power intensity distribution within the equivalent focal spot is close to an optimal energy distribution, having a shape approaching that of a rectangular distribution.

In this way, if $I_o$ is the power intensity needed to destroy the cells in a duration of 0.1 s, a peak power intensity of the order of 1.2 $I_o$ can be adopted for the focal spot. In this case, with scanning as described above, destruction of all the cells within the target is ensured.

The total energy radiated in order to destroy tissue with a power intensity distribution curve of this type is of the order of 1.2 times that theoretically necessary. The invention thus makes it possible to limit the amount of energy radiated.

In this way, it is possible to obtain an equivalent focal spot having a large diameter without causing aberrations around the ultrasound field. Ultrasound power distribution within the equivalent focal spot is such that the power radiated is almost completely employed for destruction purposes, with losses by diffusion or spreading of thermal energy being limited. The invention thus makes it possible to overcome the disadvantages of the prior art.

In another example of an embodiment of the invention, the high-frequency pilot signal generator does not deliver a periodic signal consisting of wave trains and blanks, but rather supplies a continuous signal during the shot. The position of the focal spot varies without ultrasound transmission being interrupted, with a speed or displacement pitch such that the excess energy in the power intensity diagram of FIG. 4a is used in neighboring positions. It is thus possible, like in the preceding example, to displace the focal spot every 1 ms by a distance of the order of the 6 dB diameter $r_o$. Overlap between neighboring focal spots is then of the order of 80%.

Thus, an equivalent focal spot the shape, size and energy distribution of which can be suitably adapted is formed.

The time separating each displacement of the focal spot and the distance through which the focal spot is displaced can be selected whereby the speed at which displacement occurs is higher than the speed at which thermal energy diffuses at the target, so that the power intensity profile of the equivalent focal spot has the desired shape. In this case, losses due to heat energy spreading during sweep of the region to be treated are negligible.

Figure 5A:
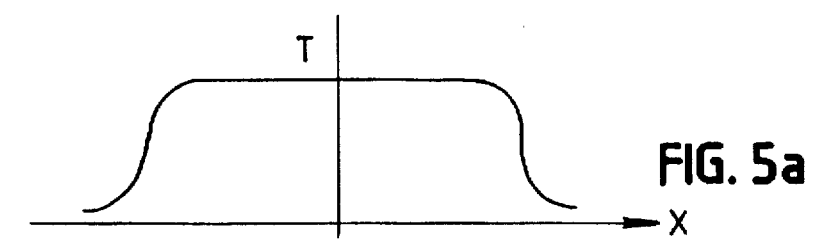
FIGS. 5a to 5c show variations in temperature with time, at a synthetic focal spot according to the invention.
Figure 5B:
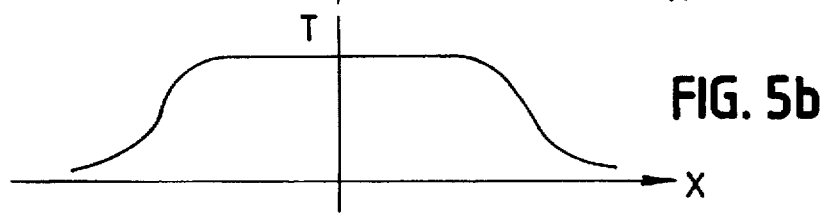
Figure 5C:
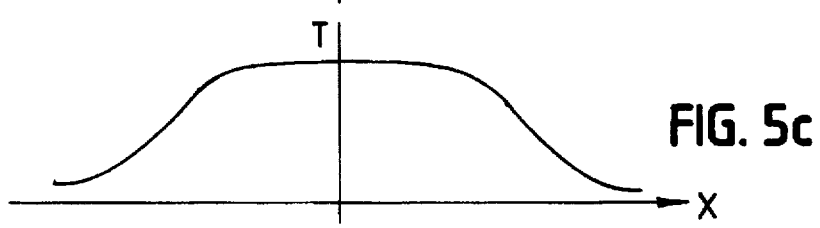

FIGS. 5a to 5c show the evolution of temperature with time at a circular equivalent focal spot after the end of a shot.

In FIGS. 5a to 5c temperature is shown on the y-axis and the distance along the semi-spherical dish axis along a straight line orthogonal to this axis, on the x-axis. FIG. 5a shows the temperature just after the end of a shot. The general shape of the curve in FIG. 5a is similar to that of FIG. 4b, temperature increase being substantially proportional to the radiated power intensity. FIGS. 5b and 5c show the temperature 2 seconds and 4 seconds after the end of the shot. FIGS. 5b and 5c highlight the effects of diffusion of thermal energy on temperature. The temperature at the edges of the equivalent focal spot drops off progressively, whereas the temperature at the center remains substantially constant.

The invention proposes, in order to limit the amount of energy radiated, and in order to maintain a constant temperature over the whole of the equivalent focal spot, to modify the power intensity distribution over the equivalent focal spot for the subsequent shots. As can be seen in FIGS. 5a–5c, the temperature drops off at the perimeter of the equivalent focal spot but remains more or less constant at the center thereof. The invention thus proposes starting, at the first shot, with a complete sweep or scan of the equivalent-focal spot and then, during subsequent shots, maintaining the temperature over the whole equivalent focal spot by only irradiating the perimeter region thereof.

Figure 6A:
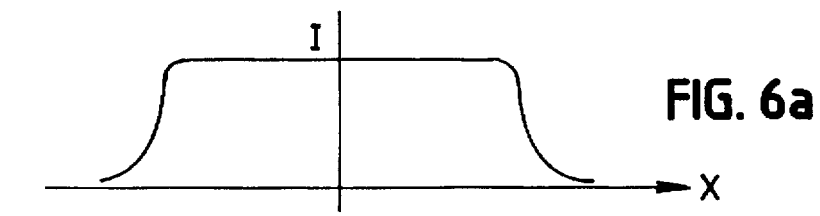
FIGS. 6a to 6c show the distribution of power intensity over the equivalent focal spot, which enables a constant temperature to be maintained.
Figure 6B:
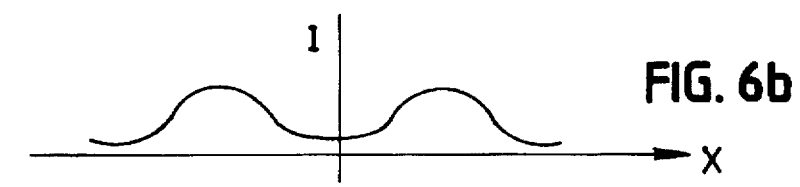
Figure 6C:
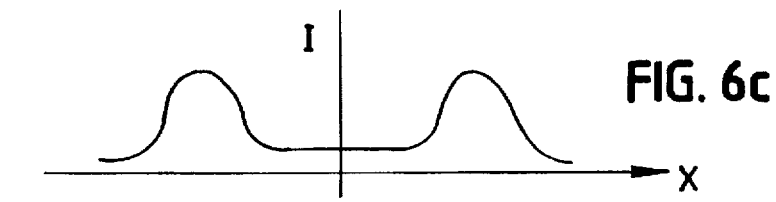

FIGS. 6a to 6c show a power intensity distribution over the equivalent focal spot for successive shots, enabling the temperature to be kept constant. FIG. 6a shows the shape for radiated power after a first shot of 0.1 s. The curve in FIG. 6a has the same shape generally as the curve in FIG. 4b, and corresponds to a homogeneous sweep of the equivalent focal spot. The curve in FIG. 6b shows the radiated power intensity for a shot occurring between 2 and 3 seconds after the first shot, and corresponds to sweeping of the perimeter region of the equivalent focal spot. The shape of the power intensity in FIG. 6b makes it possible to compensate for losses due to the spread or diffusion of thermal energy, represented in FIG. 5b. Similarly, the curve in FIG. 6c shows the radiated intensity profile in a shot between 3 seconds and 4 seconds after the first shot and corresponds to sweeping the perimeter region of the equivalent focal spot. The shape of the intensity distribution in FIG. 6c makes it possible to compensate for the losses due to diffusion of thermal energy, represented in FIG. 5c.

In this way, the invention makes it possible to limit the energy radiated to the region under treatment, so that after the first shot, only the amount of energy needed to compensate for spread of heat is delivered. It thus becomes possible to maintain a substantially constant temperature at the equivalent focal spot for substantial periods of time.

Figure 7A:
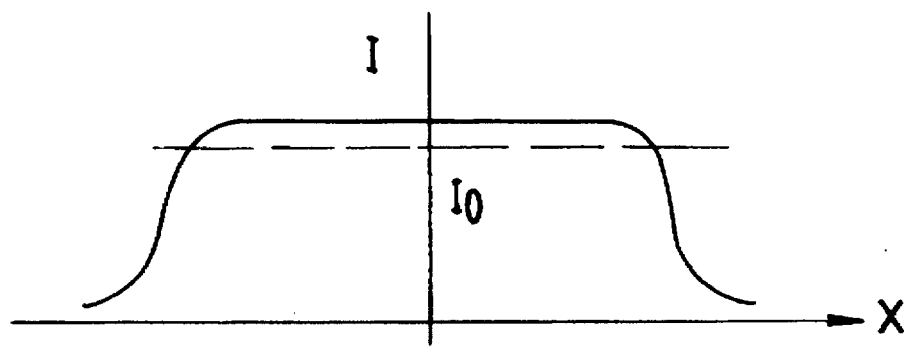
FIGS. 7a to 7c show power intensity distribution within the plane of the equivalent focal spot and in the plane situated ahead thereof.
Figure 7B:
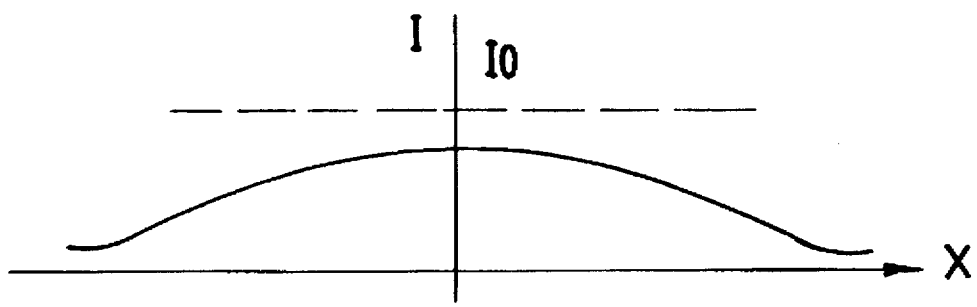
Figure 7C:
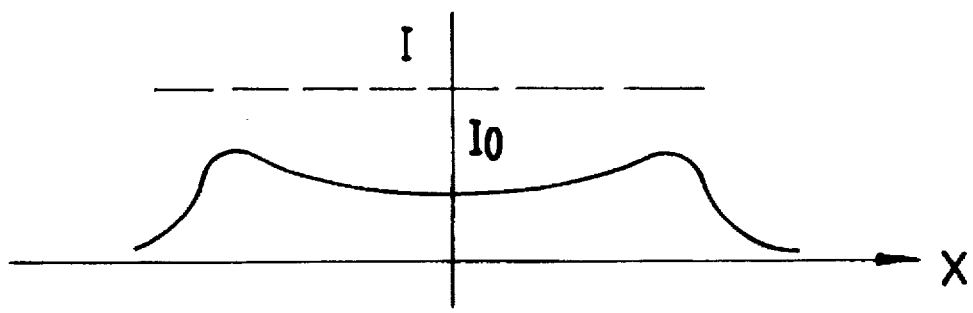

The invention also discloses the use of a similar principle when destruction of three-dimensional targets is involved. In the cases of such targets, different layers (or planes) are treated successively. FIGS. 7a to 7c show power intensity distribution in the plane of the equivalent focal spot, and in a plane forward thereof. FIG. 7a shows, after a first shot, power intensity distribution in the plane of the equivalent focal spot along a straight line passing through said equivalent focal spot. FIG. 7a is similar to FIGS. 4b or 6a. FIG. 7b shows power intensity distribution along a parallel straight line at a plane forward thereof, in other words closer to the transducer. The power level that corresponds to the destruction threshold is indicated by $I_o$ as before in FIG. 4b. As FIG. 7b shows, during the shot, a certain amount of energy is also deposited ahead of the equivalent focal spot plane The invention takes account of this fact when applying the treatment to this plane. Stated in other terms, where three dimensional targets are involved, the target is split up into layers, and one starts, with a first shot, by treating the deepest layer, the number of displacements of the focal spot being selected to cover the whole target for the layer concerned, as indicated above with reference to FIG. 4b. Once this layer has been swept in a substantially homogeneous fashion, the next layer is treated, this being a layer slightly closer to the transducer. For this layer, account is taken of the fact that the first shot led to a certain amount of energy being deposited in the layer concerned, as shown in FIG. 7b. It may be sufficient, to ensure destruction of the cells in this second layer, to suitably supplement this energy. FIG. 7c shows, and along the same straight line as the one in FIG.7b, the power intensity distribution radiated during the second shot.

In this way, a further reduction in the amount of total energy radiated to the target is achieved, while still ensuring that destruction is effective.

By way of example, if we imagine the cubic-shaped target with 10 mm sides, this target can be treated as 5 successive layers. The first layer (the deepest) is for example treated during the first shot, in 0.4 seconds uniformly sweeping the square surface using 100 displacements of the focal spot. The second layer, which is 2 mm higher, is treated immediately afterwards, with a second shot, for a duration of 0.2 s, but not using uniform sweeping of the square this time but rather as described in FIG. 7c, by more specially insonifying the edges of the square to supplement the energy deposited the second layer during the first shot. Treatment is continued in the manner described above, enabling the complete target to be treated within a duration of about one second, during which spread of heat is negligible.

This corresponds to a treatment mode in which it is desired to destroy the total volume of the target. It is also possible to only treat the surface of a three-dimensional target, to cause necrosis of its outline.

The embodiments of the invention described with reference to FIGS. 6a–6c and 7a–7c can be combined. It is thus possible to take simultaneously account for temperature evolution with time due to spread of heat and the presence of energy outside of the equivalent focal spot plane.

According to the invention, the shape of the target to be treated is determined after which the various treatment shots are simulated by computer in order to take account of diffusion of thermal energy and/or the presence of energy outside the plane of the equivalent focal spot. As the shape of the focal spot is determined in advance, the computer calculates for each position of this focal spot, the temperature obtained at the next position of the focal spot as a result of energy that has already been radiated. The computer adjusts power intensity for the next position of the focal spot so as to obtain the desired temperature. This makes it possible to determine for all points on the target, the amount of energy necessary and sufficient to ensure destruction, while simultaneously limiting the risk of burning due to excess energy.

Such computer simulation can be achieved by successive iterations, in order to take full account of the fact that each shot also reacts on the preceding shot. However, it should be noted that if the power intensity has been adjusted correctly, the tissues may be destroyed during the first pass and under these conditions, as the ultrasound, is poorly transmitted in the regions that are burned. Subsequent shots have little effect on zones that are already burned, which simplifies calculation. Other methods of calculation and simulation can also be envisaged.

Obviously, it is possible to modify the distribution of the energy radiated, regardless of the shape of the equivalent focal spot, this not being limited to the cubic or circular shapes discussed above by way of illustration, in order to provide suitable adaptation to losses due to spread of heat; it is thus possible to maintain the temperature constant over the whole equivalent focal spot or the volume of the target, by limiting the amount of energy radiated. This furthermore makes it possible to limit the temperature increase outside of the equivalent focal spot.

To allow for variation of power intensity at the equivalent focal spot, which may be necessary for this type of treatment, it is possible to introduce variation of the displacement step or pitch between each position of the focal spot. As described above, optimum overlap of the equivalent focal spot is obtained when the step is equal to the 6 dB diameter of the focal spot.

It is also possible to vary the duration of the excitation signal for a given position of the focal spot; in the example given above, this duration is 1 ms but it can for example vary in a range of from 0.1 ms to 20 ms.

The minimum duration is dictated by the fact that a wave train must include a sufficient number of oscillations for operations corresponding to permanent running to be achieved for a time well in excess of the transitory operating conditions that prevail at the beginning and end of a wave train, meaning:

the amplitude and waveform of the wave delivered has stabilized, i.e. after 4 to 5 oscillations for well-matched ceramic, equivalent to about 4 to 5 μs for 1 MHz;

considerable overlap of the wave trains from different ceramics at the focus in the most unfavorable case, i.e. about 5 μs, equivalent to 5 oscillations at 1 MHz.

Under these conditions, operation under transitional conditions lasts at the most about 10 μs. The minimum duration of 0.1 ms thus ensures effective treatment.

Regarding now the maximum duration of transmission at a given position of the focal spot, the total volume to be treated during a shot should of course be swept in a period that is sufficiently brief for diffusion of thermal energy not to substantially modify temperature distribution. For instance, as a function of volume, a total duration of 1 to 5 seconds may be suitable. This duration will depend on the number of points and on the duration of transmission at each point.

This is a way of determining the duration of transmission at each point on the focal spot. For 1,000 points, this duration can extend up to 1 ms; for 100 points, it can reach 10 ms. A choice of 20 ms for the maximum duration is hence reasonable.

Finally, it is possible to vary the duration of the blank intervals during which the position of the focal spot is changing, where such blank intervals are employed.

The invention thus makes it possible to modify the intensity of radiation, without this implying variations in the amplitude of the excitation signals and of the ultrasound signals delivered by the piezoelectric elements. This leads to considerable simplification of the structure of the device employed.

Figure 8:
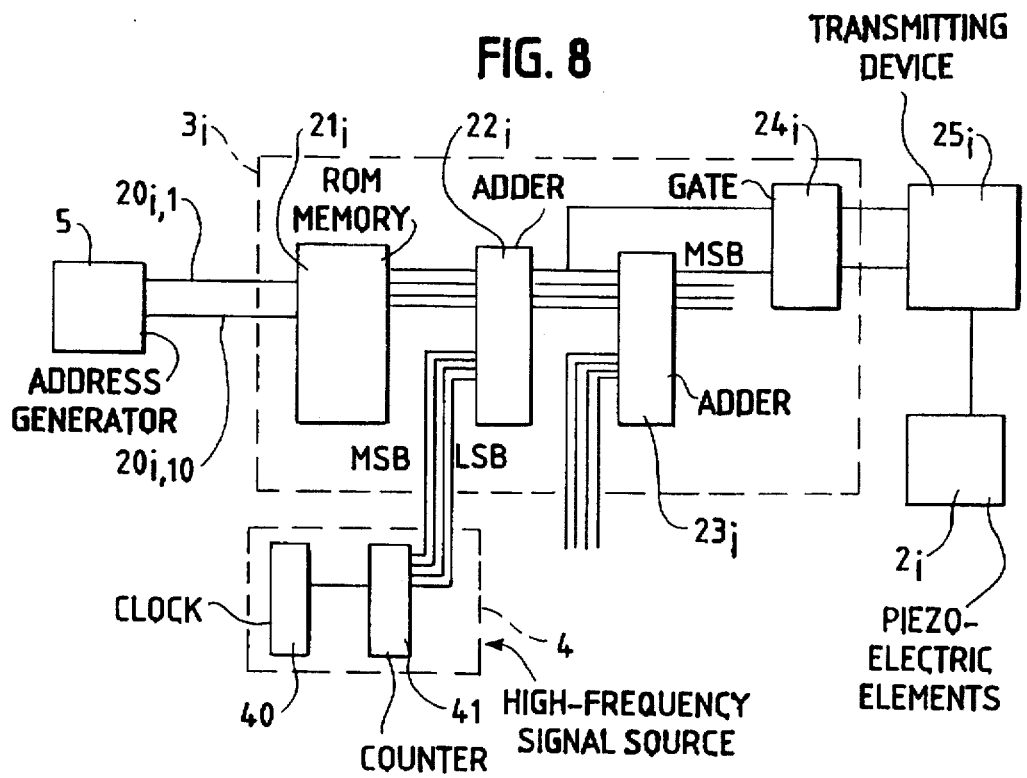
FIG. 8 is a block diagram of another embodiment of the device in FIG. 1.

FIG. 8 shows a block diagram of a further embodiment of the device shown in FIG. 3. Here, transmitter $3_i$ in FIG. 8 receives, from address generator 5, an address signal giving the position of the focus on 10 bits, over a plurality of lines $20_{i,1}$ to $20_{i,10}$.

It also receives a high-frequency pilot signal from source 4. If f is the transmission frequency of the ultrasound signal, the signals from the piezoelectric elements are put out of phase, as explained above, by a multiple of one sixteenth of the phase. High-frequency pilot signal generator 4 includes a clock 40 of frequency 16×f driving a four-bit decimal counter 41. At the output from counter 41, the most significant bit (MSB) thus supplies a square wave signal of frequency f.

Transmitter $3_i$ includes memory means, for example ROM memory $21_i$ (or any other type of memory), which is supplied with signals indicating the position of focus on lines $20_{i,1}$ to $20_{i,10}$ and supplying a phase-shift signal on four bits at its output.

Transmitter $3_i$ comprises a 2×4 bit adder $22_i$ which receives of one of its inputs the four bits output from ROM memory $21_i$ and the four bits from the counter 41 of high-frequency pilot frequency source 4 on its other input (optionally via a supplementary gate as described below with reference to FIG. 10). In this way, on the MSB at the output of adder $22_i$, the clock signal of frequency f is obtained with a delay corresponding to the phase shift given by ROM memory $21_i$.

Transmitter $3_i$ comprises a second 2×4 bit adder $23_i$, enabling a second constant phase shift to be introduced. Adder $23_i$ receives the output from adder $22_i$ on one of its inputs and a four bit signal on its other input enabling the idle time between two control signals to be varied. The control signal giving the idle time has a set amount for all the piezoelectric elements, depending on the idle time separating two push-pull transistor drive signals for a transmitter device $25_i$ associated with a piezoelectric element $2_i$.

Transmitter $3_i$ includes a gate $24_i$ which receives the MSB from the output of adder $22_i$ and the MSB supplied from the output of adder $23_i$, at its input. The AND and NOR outputs of gate $24_i$ control transmission device $25_i$, by supplying the push-pull transistor drive signals.

Figure 9:
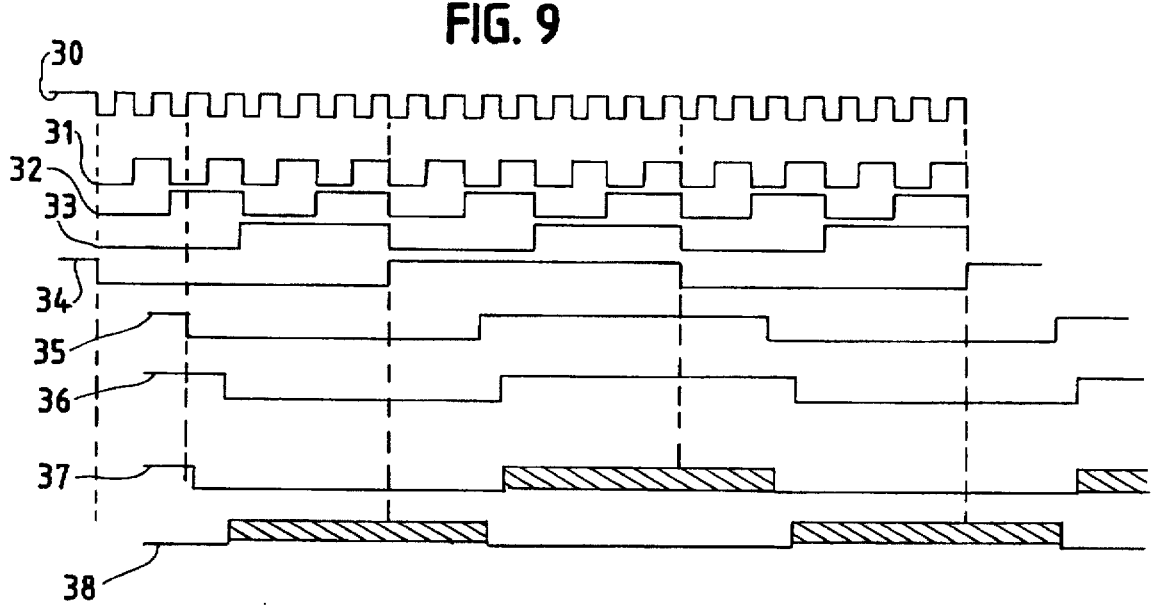
FIG. 9 is a timing diagram of the signals in the circuit in FIG. 8.

FIG. 9 shows a timing diagram of the signals in the circuit in FIG. 8. In FIG. 9, there can be seen signal 30 having a frequency 16×f delivered by clock 40; the signals 31 to 34 output from counter 41, signal 34 corresponding to the MSB of frequency f; signal 35 for the MSB at the output from adder $22_i$, phase-shifted with respect to the delay signal 34 supplied by the memory $21_i$; signal 36 for the MSB output by adder $23_i$, phase-shifted with respect to signal 35 by a value equal to the idle and the signals 37 and 38 output by gate $24_i$.

The circuit in FIG. 8 is simple and highly stable. Its simplicity enables it to easily be reproduced in large numbers, for each piezoelectric element of the transducer.

The operation of the circuit in FIG. 8 is stable as the values of the delays are applied permanently and are only modified when the position of the focus changes; it is thus possible to apply a vigorous filtering to the signals corresponding to the delays. Similarly, if the value should get modified as a result of a powerful interference spike or similar, the interference can only be transitory.

Figure 10:
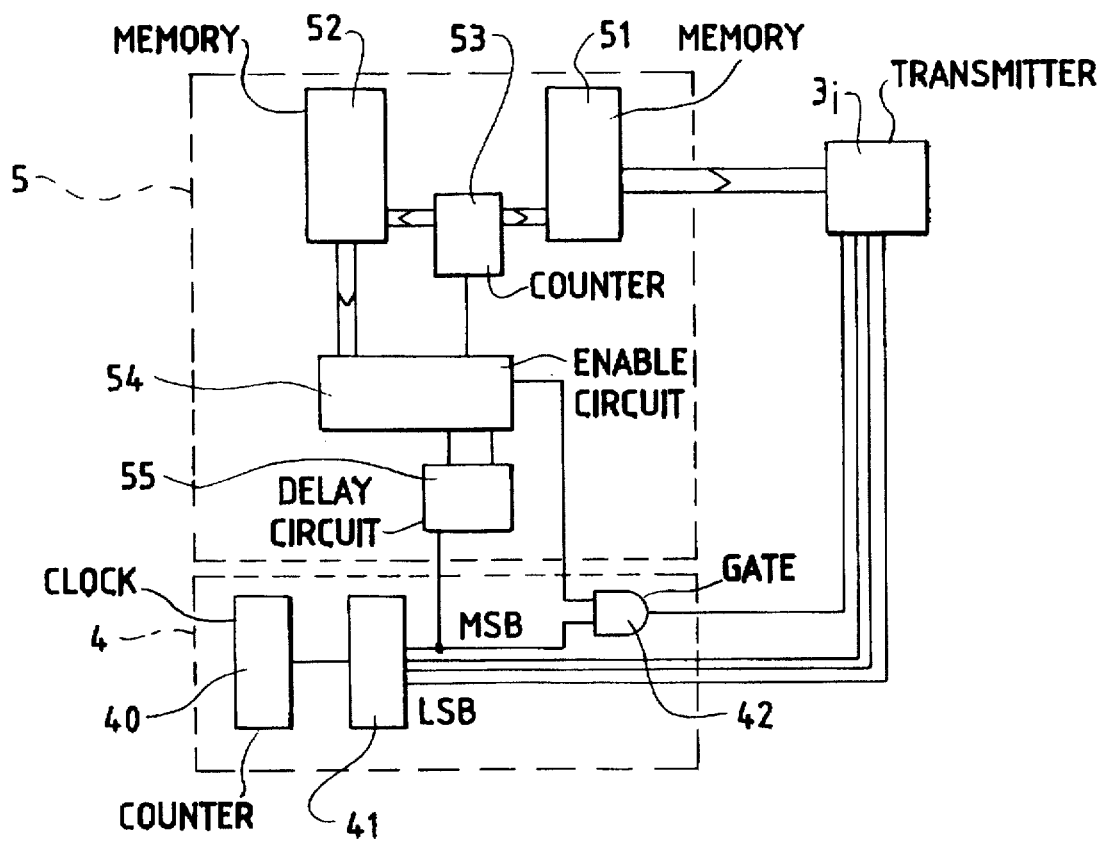
FIG. 10 is a block diagram of a further embodiment of an apparatus for carrying out the invention.

FIG. 10 shows another embodiment of apparatus for carrying out the invention. In FIG. 10, the high-frequency signal generator 4, the clock 40 operating at 16×f and the counter 41 can be seen.

Before starting treatment, the parameters of the treatment—total firing time, successive positions of the focal spot and duration of ultrasound transmission for each position of the focal spot—obtained for example by computer simulation, are supplied to two reprogrammable memories (RAM or EEPROM) 51 and 52 of address generator 5.

Address generator 5 includes a counter 53 permanently containing the number specifying the current position of the focal spot with respect to all the successive positions of the focal spot. Counter 53 permanently supplies memories 51 and 52 with a signal representing the current position of the focal spot.

During treatment, memory 51 supplies the various transmitters $3_i$ with the addresses of the current position of the focal spot, as explained above, on the lines $8_{i,1}$ to $8_{i,n}$ (FIG. 3) or $20_{i,1}$ to $20_{i,10}$ (FIG. 10).

Address generator 5 further includes an enable circuit 54 and a delay circuit 55. Enable circuit 54 receives a digital signal supplied by the memory 52 representing the duration of ultrasound transmission and the current position of the focal spot.

The enable circuit 54 further receives a clock signal from clock 40 at a frequency f, via the delay circuit 55 and counter 41.

Figure 11:
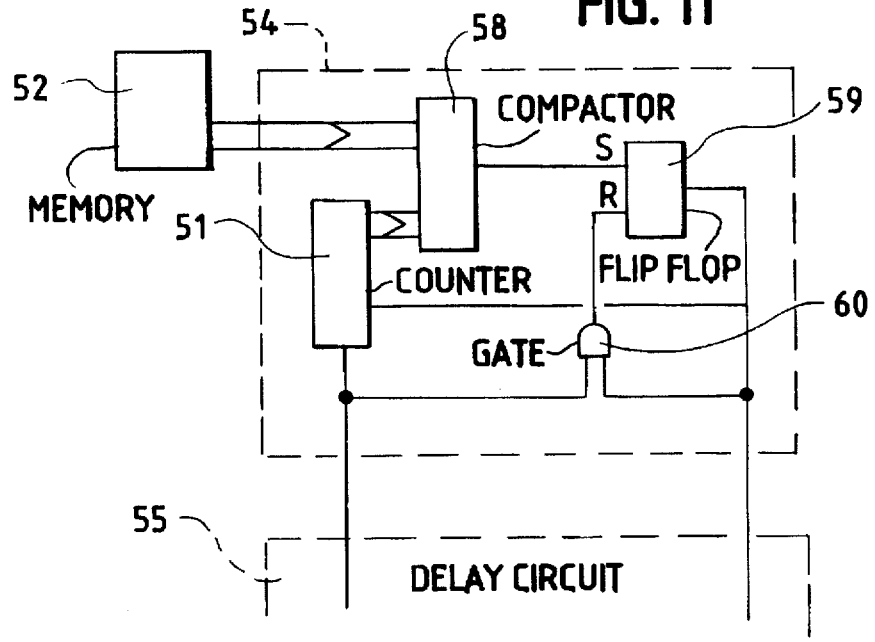
FIG. 11 is a more detailed block diagram of one embodiment of the enable circuit of FIG. 10.

The enable circuit 54, the internal structure of which is shown in FIG. 11, contains a counter 57 and a comparator 58. The enable circuit 54 carries on counting over a duration corresponding to the duration signal supplied by the memory 52, and outputs an enabling signal. When the value output from the counter of the enable circuit 54 reaches the target value supplied by the memory 52, enable circuit 52 stops supplying the enable signal. The enable circuit's counter is then reset, and delay circuit 55 inhibits the clock signal supplied by clock 41. Moreover, the fact that the enable signal has ceased to be present is applied to the counter 53 containing the number specifying the current position of the focal spot to indicate that delivery of ultrasound has stopped at the specific position of the focal spot; counter 53 then supplies memories 51 and 52 with a signal giving the next serial number for the position of the focal spot. The memories 51 and 52 then supply the corresponding position and the corresponding duration.

After an interval of adjustable duration, the delay circuit 55 again allows the clock signal to reach enable circuit 54.

An AND gate 42 receives the enable signal applied by enable circuit 54 at its input together with the MSB from counter 40. The output from the AND gate 42 is supplied to the transmitters $3_i$, as a clock signal of frequency f. In this way, the transmitters only receive a signal, the most significant bit of which corresponds to the clock signal, over periods corresponding to the duration of ultrasound transmission. The transmitters $3_i$ receive a signal the other bits of which (least significant bits) are supplied by the counter 41.

Delay circuit 55 makes it possible, firstly, to eliminate all transmission while the focal spot is being switched from one position to another and, secondly, to allow adjustment, if necessary, of mean power by increasing or decreasing the interval between ultrasound transmission, between two positions of the focal spot.

FIG. 11 is another more detailed block diagram of an embodiment of the enable circuit 54 of FIG. 10. Here, enable circuit 54 includes a counter 57 receiving the clock signal originating from delay circuit 55. The output from counter 57 is supplied to one input of the comparator 58 the other input of which receives the duration signal originating from memory 52. The output from the comparator 58 is supplied to the S input of a RS flip-flop 59, which supplies the enable signal from enable circuit 52 at its output. In this way, the output from flip-flop 59 is reset when the value supplied by the counter reaches the ultrasound transmission duration supplied by memory 52.

The output signal from flip-flop 59 is additionally supplied to delay circuit 55, in order to trigger the delay following transmission. This output signal is additionally applied to one input of a gate 60 the other input of which receives the signal from delay circuit 55, the output from this gate being supplied to the R input of flip-flop 59. Thus, the gate is reset to enable the flip-flop to be set to "1". The output signal from flip-flop 59 is additionally applied to the reset input of counter 57, for resetting the counter at the end of a transmission. When delay circuit 55 stops blocking the clock signal, the first clock signal edge sets the flip-flop to "1", thus re-starting the counter.

The devices shown in FIGS. 8 to 11 make it possible to implement the invention using simple and stable circuits.

Figure 12:
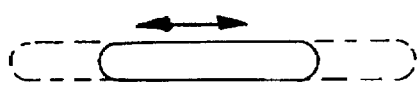
FIG. 12 shows one possible shape of a focal spot and an equivalent focal spot according to the invention.

FIG. 12 shows one possible shape of the focal spot and the equivalent focal spot according to the invention. The focal spot and the equivalent focal spot in FIG. 12 have an elongated shape and make it possible to limit, even more the effects of the region being treated which may be moving. The focal spot is shown in solid lines on FIG. 12: it has an elongated shape obtained, for example, in an apparatus such as that shown in FIGS. 2 and 3 by applying phase-shifting to certain transmitters $3_i$. Advantageously, the focal spot is elongated in the direction of movement of the region to be treated. Because of this, the ratio between the swept surface and the surface area of the equivalent focal spot is smaller than would be the case if the focal spot were circular, and the influence of the region being treated moving is reduced.

According to the invention, the treatment apparatus is controlled in the following manner. First, using known means, the position and the dimensions of the target to be treated are determined. Following this, the number of layers needed for treatment is determined, and the shape of the target in each layer is determined.

Depending on the nature of the target and on the depth of treatment, the frequency of the ultrasound treatment waves is then determined.

Next, a size and, if appropriate, a shape for the equivalent focal spot is chosen, this being done, if necessary, for each layer. Next, for this equivalent focal spot, the duration of treatment and the ultrasound power necessary to ensure cell destruction are determined. Treatment can then proceed as in the prior art. However, the disadvantages of the prior art are avoided, and for example those related to scanning or sweeping a moving target. Here, the equivalent focal spot according to the invention is created at such a high speed that movements of the target are negligible.

The treatment time, in a prior art device having a focal spot of a diameter of about 2 mm, is typically of the order of 0.1 seconds, for an ultrasound frequency of 1 MHz and an acoustic power of the order of 10 kW. This 0.1 seconds duration is below the stabilization time which is of the order of 2 seconds (the period of time after which loss of heat due to diffusion of thermal energy compensates the energy supplied by the ultrasound waves).

For a larger equivalent focal spot, the stabilization time increases in line with the ratio of the diameters; thus, in the example above of an equivalent focal spot having a surface area fifty times larger than the focal spot itself and having a diameter of some 15 mm, the stabilization time is of the order of 15 seconds. Due to the increase in energy yield, the time needed to destroy the cells inside the equivalent focal spot is not multiplied by fifty, but is of the order of 2.5 seconds, for an equivalent frequency and power. In this way, the treatment time according to the invention is still below the stabilization time. This time is also sufficiently small for the apparatus not to be substantially affected by movements of the treatment region.

Obviously, the present invention is not limited to the embodiments described and shown but may undergo numerous modifications available to those skilled in the art without departing from the scope of the invention. Thus, the sweep or scanning for producing the equivalent focal spot from the focal spot can be done in very many ways. The focal spot can move in one plane, or it can also move in space. The equivalent focal spot can have a spherical shape or even, an elliptical shape and, more generally, any two- or three-dimensional shape.

Finally, it is clear that delay lines or any other equivalent mechanism can be used to move the focal spot in place of the phase-shifting devices. Thus "phase variation" should be taken to cover the case where delay equivalent to phase variation is employed. It is also possible, notably in the case of small transducers, to vary the position of the focal spot with respect to the transducer by mechanical devices such as moving mirrors or prisms. It is also possible to mechanically move the complete transducer with the spot moving in this case relative to the means supporting the transducer which are generally fixed with respect to the patient being treated. Regardless of the system chosen, it will be clear that the invention involves moving the focal spot with respect to the region to be treated, this being able to be achieved by different means.

What is claimed is:

1. A method for controlling an ultrasonic hyperthermia treatment apparatus having a transducer with a plurality of piezoelectric elements, each element excited by an electrical signal, the method comprising the steps of:
    a) emitting ultrasound focused at a focal spot;
    b) varying a position of said focal spot during a shot, with respect to said transducer to cause a region to be treated to be scanned by the focal spot such that a plurality of positions of the focal spot defines an equivalent focal spot;
    c) the speed of variation of the position of said focal spot with respect to said transducer is higher than the speed of diffusion of thermal energy in the region to be treated; and
    d) the peak power of the focal spot and the degree of overlap between the plurality of positions of said focal spots are arranged such that, during the shot, the energy radiated at every point in the region scanned by varying the position of said focal spot with respect to said transducer is substantially equal to the energy needed to destroy tissue cells in the region to be treated.

2. A method according to claim 1, wherein said equivalent focal spot is homogeneously scanned during a shot.

3. A method according to claim 2, wherein the ultrasound energy is delivered, during a shot, in the form of wave trains separated by blank intervals, and wherein the position of said focal spot varies with respect to the transducer during said blank intervals.

4. A method according to claim 2, wherein the ultrasound energy is delivered, during one shot, in the form of continuous wave trains and wherein the position of said focal spot varies with respect to the transducer without delivery of ultrasound energy being interrupted.

5. A method according to claim 1, wherein said equivalent focal spot is scanned in a non-homogeneous manner during a shot in order to supplement energy supplied during one or several preceding shots.

6. A method according to claim 5, wherein the ultrasound energy is delivered, during a shot, in the form of wave trains separated by blank intervals, and wherein the position of said focal spot varies with respect to the transducer during said blank intervals.

7. A method according to claim 5, wherein the ultrasound energy is delivered, during one shot, in the form of continuous wave trains and wherein the position of said focal spot varies with respect to the transducer without delivery of ultrasound being interrupted.

8. A method according to claim 1, wherein said focal spot has an elongated shape and is displaced with respect to the transducer substantially along its longitudinal direction.

9. A method for controlling an ultrasonic hyperthermia treatment apparatus having a transducer with a plurality of piezoelectric elements, each element excited by an electrical signal, the method comprising the steps of:
   a) emitting ultrasound focused at a focal spot;
   b) varying a position of said focal spot during a shot, with respect to said transducer to cause a region to be treated to be scanned by the focal spot such that a plurality of positions of the focal spot defines an equivalent focal spot;
   c) the speed of variation of the position of said focal spot with respect to said transducer is higher than the speed of diffusion of thermal energy in the region to be treated;
   d) the variation of the position of said focal spot with respect to said transducer solely due to variation in relative phases of the electrical signals exciting said piezoelectric elements; and
   e) the peak power of the focal spot and the degree of overlap between the plurality of positions of said focal spot are such that, during the shot, the energy radiated at every point in the region scanned by varying the position of said focal spot with respect to said transducer is substantially equal to the energy needed to destroy tissue cells in the region to be treated.

10. A method according to claim 9, wherein said equivalent focal spot is homogeneously scanned during a shot.

11. A method according to claim 10, wherein the ultrasound energy is delivered, during a shot, in the form of wave trains separated by blank intervals, and wherein the position of said focal spot varies with respect to the transducer during said blank intervals.

12. A method according to claim 10, wherein the ultrasound energy is delivered, during one shot, in the form of continuous wave trains and wherein the position of said focal spot varies with respect to the transducer without delivery of ultrasound energy being interrupted.

13. A method according to claim 9, wherein said equivalent focal spot is scanned in a non-homogeneous manner during a shot in order to supplement energy supplied during one or several preceding shots.

14. A method according to claim 13, wherein the ultrasound energy is delivered, during a shot, in the form of wave trains separated by blank intervals, and wherein the position of said focal spot varies with respect to the transducer during said blank intervals.

15. A method according to claim 13, wherein the ultrasound energy is delivered, during one shot, in the form of continuous wave trains and wherein the position of said focal spot varies with respect to the transducer without delivery of ultrasound energy being interrupted.

16. A method according to claim 9, wherein said focal spot has an elongated shape and is displaced with respect to the transducer substantially along its longitudinal direction.

17. A hyperthermia treatment apparatus comprising:
   a) a transducer with a plurality of piezoelectric elements, each element excited by an electrical excitation signal, the transducer having a focus spot;
   b) a transmitter for generating each said electrical excitation signal;
   c) each said transmitter receiving an identical high-frequency pilot signal from a common source, and each said transmitter receiving an address from an address generator;
   d) each said transmitter further including means for shifting the phase of said received high-frequency pilot signal as a function of an address received from the address generator to provide the electrical excitation signal to the piezoelectric elements; and
   e) said means for shifting the phase configured to cause the position of the focus spot to vary, and configured to cause a degree of overlap between the focus spots to vary such that a speed of variation of the position of said focal spots is higher than the speed of diffusion of thermal energy in the region to be treated.

18. The hyperthermia treatment apparatus according to claim 17, wherein in each one of said transmitters, said means for shifting the phase of said pilot signal comprises a shift register and memory means operatively coupled to the shift register for controlling the shift register as a function of the address received from said address generator, said memory means being pre-programmed as a function of the position of the transmitter relative to an object to be treated.

19. A hyperthermia treatment apparatus according to claim 18, wherein each one of said shift registers shifts the phase of said pilot signal varying in one-sixteenth of a period steps.

20. A hyperthermia treatment apparatus according to claim 18, wherein each one of said shift registers shifts the phase of said pilot signal varying in one-eighth of period steps.

* * * * *